US007219874B2

(12) United States Patent
Tippett

(10) Patent No.: US 7,219,874 B2
(45) Date of Patent: May 22, 2007

(54) ACCESS FITTING FOR GAS SAMPLING BAG

(75) Inventor: John W. Tippett, Boston, MA (US)

(73) Assignee: Textiles Coated International, Amherst, NH (US)

( * ) Notice: Subject to any disclaimer, the term of this patent is extended or adjusted under 35 U.S.C. 154(b) by 863 days.

(21) Appl. No.: 10/658,942

(22) Filed: Sep. 10, 2003

(65) Prior Publication Data

US 2005/0050967 A1    Mar. 10, 2005

(51) Int. Cl.
*F16K 35/00*    (2006.01)

(52) U.S. Cl. ............... 251/89.5; 251/901; 222/561; 141/68; 383/66

(58) Field of Classification Search ........... 141/10, 141/68, 314; 251/89.5, 170, 193, 194, 195, 251/149.9, 901, 90; 222/80, 81, 541.2, 561; 604/403–416; 383/66, 80, 904, 906, 352; 73/864.74, 864.62

See application file for complete search history.

(56) References Cited

U.S. PATENT DOCUMENTS

| 3,143,109 | A | | 8/1964 | Gewertz |
| 3,581,573 | A | * | 6/1971 | Purcell et al. ............ 73/863.11 |
| 3,707,239 | A | | 12/1972 | Harris, Sr. et al. |
| 3,757,981 | A | | 9/1973 | Harris, Sr. et al. |
| 4,270,677 | A | * | 6/1981 | Schmidt .................... 222/561 |
| 4,449,649 | A | * | 5/1984 | Flannigan ................ 222/181.3 |
| 5,456,126 | A | | 10/1995 | Suddath |
| 6,055,872 | A | | 5/2000 | Little |
| 6,904,662 | B2 | * | 6/2005 | Thibault et al. ............. 29/511 |

* cited by examiner

*Primary Examiner*—Eric Keasel
*Assistant Examiner*—John K. Fristoe, Jr.
(74) *Attorney, Agent, or Firm*—Gauthier & Connors, LLP

(57) ABSTRACT

An access fitting has a housing with a base and a cap located respectively on interior and exterior sides of the wall of a gas sampling bag. The base and cap are provided respectively with inner and outer ports aligned with an opening in the bag wall to provide a through passageway communicating with the interior of the bag. A septum is interposed between the cap and the exterior side of the bag wall. The septum has a hole therein and is slidably adjustable between an open position at which its hole is aligned with the through passageway, and a closed position at which its hole is removed from the through passageway and the through passageway is blocked by an imperforate segment of the septum. A tubular connector is received in the outer port, and is axially adjustable between an advanced position frictionally resisting sliding adjustment of the septum, and a retracted position accommodating such adjustment.

14 Claims, 2 Drawing Sheets

ACCESS FITTING FOR GAS SAMPLING BAG

BACKGROUND OF THE INVENTION

1. Field of the Invention

This invention relates generally to gas sampling bags, and is concerned in particular with a new and improved fitting for sealing and gaining access to an opening in the bag wall.

2. Description of the Prior Art

The lowest cost and most commonly used gas sampling bags are fabricated from Tedlar with polypropylene access fittings. However, the reusability of such bags is limited due to gas adsorption on the surface of the Tedlar material, which could adversely affect sensitive testing of subsequent gas samples.

All perfluoroplastic gas sampling bags, i.e., those fabricated from perfluoroalkoxy (PFA), fluorinated ethlylene propylene (FEP) or polytetrafluorethylene (PTFE) are also available, but at a much higher cost, due primarily to their complicated and expensive access valves that are typically machined from perfluoroplastics or stainless steel. These materials resist surface adsorption of the gases being sampled, thus making is possible to use the sampling bags repetitively. However, this advantage is compromised by the limited septum life of the access fittings.

SUMMARY OF THE INVENTION

One objective of the present invention is to provide a simpler less costly perfluoroplastic access fitting that can be used in conjunction with perfluoroplastic bag material to provide a sampling bag priced competitively with the lower cost Tedlar bags currently in use.

Another objective of the present invention is to provide an access fitting with a shiftable septum that can be repetitively punctured at different locations, thus beneficially extending the useful life of the access fitting and its associated sampling bag.

Still another objective of the present invention is the provision of an access fitting having its most expensive component detachable for reuse with other fittings.

These and other objectives, features and advantages will now be described in greater detail with reference to the accompanying drawings wherein:

DETAILED DESCRIPTION OF PREFERRED EMBODIMENTS

Figure 1:
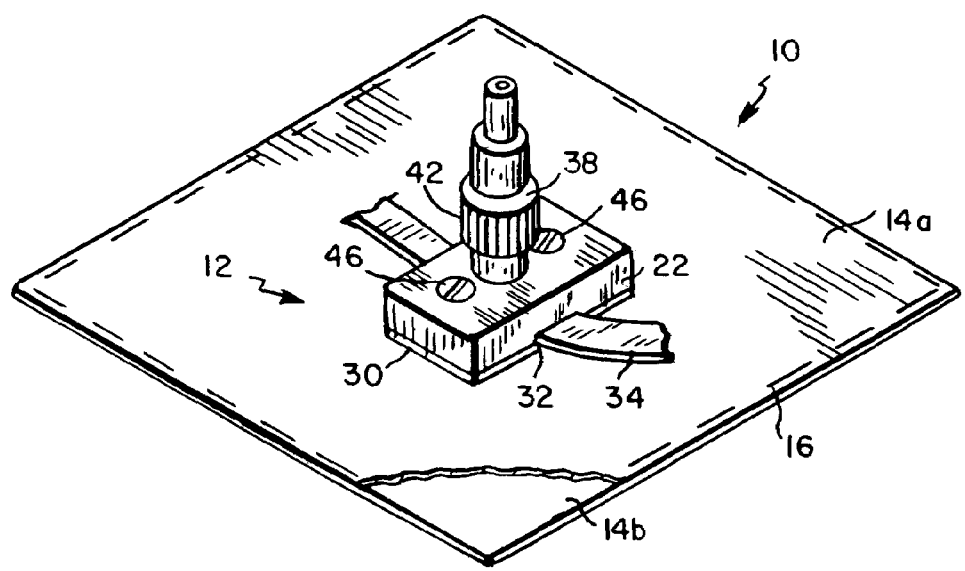
FIG. 1 is a perspective view of a gas sampling bag equipped with an access fitting in accordance with the present invention.

With reference initially to FIG. 1, a gas sampling bag is shown at 10 equipped with an access fitting 12 in accordance with the present invention.

The bag is comprised of two walls 14a and 14b of flexible material sealed as at 16 along their peripheral edges. The bag material can be selected from any of the materials currently available, preferably perfluoroplastic material such as PFA, FEP or PTFE, and most preferably a multilayer PTFE composite available from Textiles Coated International of Amherst, N.H. under the trade name "LFP".

Figure 2:
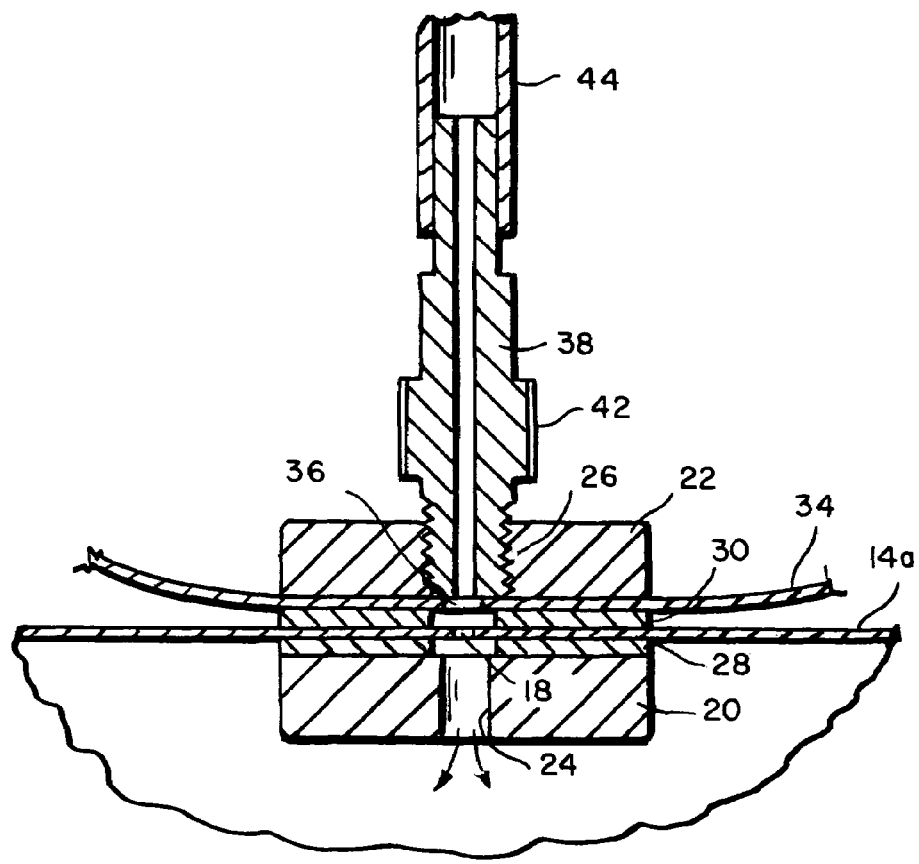
FIG. 2 is a sectional view on an enlarged scale taken through the access fitting shown in FIG. 1 with the septum slidably adjusted to its open position to accommodate filling of the bag with a gas sample.
Figure 3:
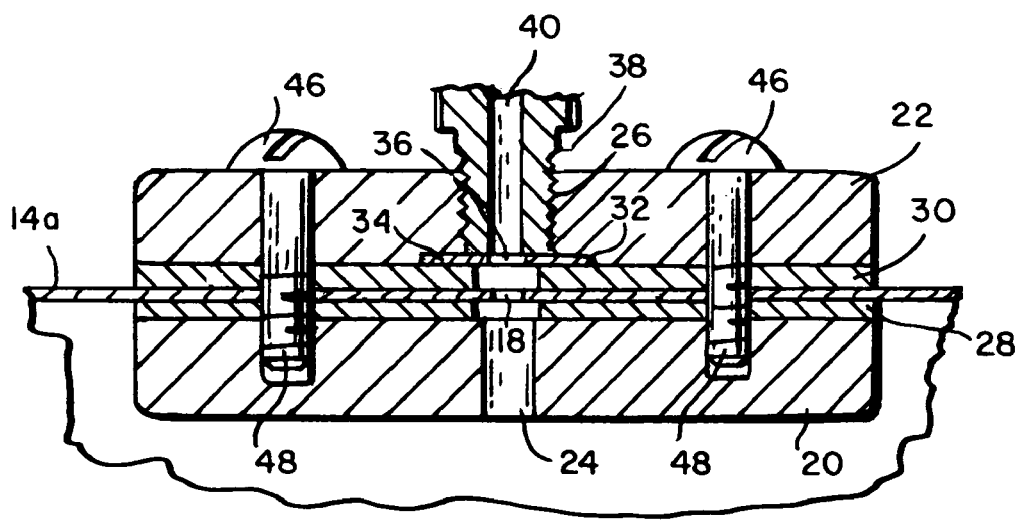
FIG. 3 is a sectional view through the access fitting at a 90° angle with respect to FIG. 2.
Figure 4:
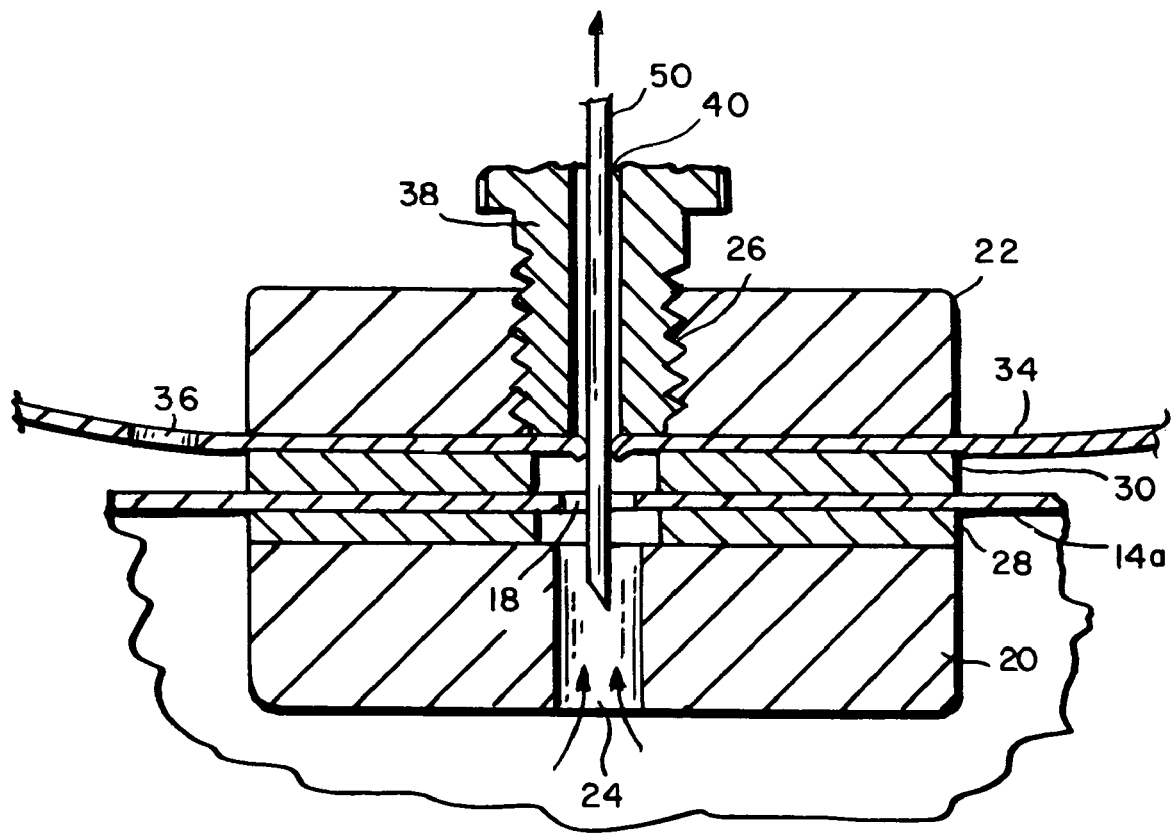
FIG. 4 is a sectional view similar to FIG. 2 showing the septum shifted to its closed position and punctured by a needle during removal of a gas sample previously charged into the bag.

With reference additionally to FIGS. 2-4, it will be seen that the upper wall 14a has an opening 18. The access fitting includes a housing having a base 20 and a cap 22 located respectively on interior and exterior sides of the bag wall 14a. The base and cap are provided respectively with inner and outer ports 24, 26 aligned with the opening 18 to provide a thorough passageway communicating with the bag interior.

Preferably, an interior sealing gasket 28 is interposed between the base 20 and the interior of the side wall 14a, and an exterior sealing gasket 30 is interposed between the exterior of the side wall and the cap 22.

The underside of the cap 22 is provided with a channel groove 32 configured and dimensioned to receive an elongated septum 34. The septum has a through hole 36 and is slidably adjustable between an open position as shown in FIGS. 2 and 3 at which the hole 36 is aligned with the through passageway defined by ports 24 and 26 and the opening 18, and a closed position as shown in FIG. 4, at which the hole 36 is removed from the through passageway, the latter being blocked by an imperforate segment of the septum.

A tubular connector 38 is threaded into the outer port 26. The connector has a through bore 40, an enlarged diameter mid section 42, and a reduced diameter upper end dimensioned detachable for connection to a supply tube 44 (see FIG. 2). The connector 42 is rotatably and axially adjustable between an advanced position as shown in FIG. 4 at which it bears against the septum to frictionally resist its slidable movement, and a retracted position as shown in FIGS. 2 and 3, at which it is spaced from the septum to thereby accommodate its sliding adjustment.

The cap 22 is connected to the base 20 by fasteners, e.g., screws 46 or the like, extending through the cap, wall 14a and gaskets 28, 30 into threaded engagement in blind bores 48 in the base. The fasteners 46 are thus isolated by the base 20 and gaskets 28, 30 from gases contained in the sample bag.

Preferably, at least the base 20, gaskets 28, 30, septum 34 and connector 38 are formed from a perfluoroplastic material. Most preferably, that perfluoroplastic material is PTFE, with the gaskets 28, 30 comprising expanded PTFE.

In use, as shown in FIGS. 2 and 3, the connector 38 is retracted and the septum is slidably adjusted to its open position. The gas to be sampled is delivered via the tubing 44 to the bag interior, after which the septum is slidably adjusted to is closed position as shown in FIG. 4, with the connector then having been advanced to frictionally resist any further movement of the septum.

The tubing 44 can then be removed, and the sample bag delivered to a laboratory for analysis of the gas sample. Gas can be removed from the bag via a needle 50 which punctures the septum, as shown in FIG. 4.

The sampling bag can be reused repetitively, with each use involving the puncturing of the septum at a different location along its length.

The fitting may be disassembled to replace a worn septum. The connector 38 comprises the most expensive component of the fitting. It can be readily separated for reuse in other fitting assemblies.

In light of the foregoing, it will now be appreciated by those skilled in the art that various changes and modifications may be made to the embodiment herein chosen for purposes of disclosure, without departing from the spirit and scope of the invention. By way of example only, the tubular connector 38 could be redesigned for snap fit engagement into and out of its advanced and retracted positions. Any convenient and readily available fasteners may be employed in place of the disclosed screws 46.

I claim:

1. An access fitting for an opening in the wall of a gas sampling bag, said fitting comprising:
   a housing having a base and a cap located respectively on interior and exterior sides of said wall, said base and said cap being provided respectively with inner and outer ports aligned with said opening to provide a through passageway communicating with the interior of said bag;
   a septum interposed between said cap and the exterior side of said wall, said septum having a hole therein and being slidably adjustable between an open position at which said hole is aligned with said passageway, and a closed position at which said hole is removed from said passageway and said passageway is blocked by an imperforate segment of said septum; and
   a tubular connector received in said outer port, said connector being axially adjustable between an advanced position frictionally resisting sliding adjustment of said septum, and a retracted position accommodating such adjustment.

2. The access fitting of claim 1 further comprising an interior gasket interposed between said base and the interior side of said wall.

3. The access fitting of claims 1 or 2 further comprising an exterior gasket element interposed between said cap and the exterior side of said wall.

4. The access fitting of claim 3 wherein said septum is slidably interposed between said cap and said exterior gasket element.

5. The access fitting of claim 1 wherein said tubular connector is threaded into said outer port and is rotatably adjustable between said advanced and retracted positions.

6. The access fitting of claims 1 or 5 wherein said tubular connector bears against said septum when in its advanced position.

7. The access fitting of claim 1 further comprising gasket elements interposed between said wall and said base and cap, said base, gasket elements, septum and connector being formed from a perfluoroplastic material.

8. The access fitting of claim 7 wherein said perfluoroplastic material is polytetrafluoroethylene.

9. The access fitting of claim 8 wherein said gasket elements are formed from expanded polytetrafluoroethylene.

10. The access fitting of claim 1 wherein said cap is connected to said base by fasteners extending through said wall.

11. The access fitting of claim 10 wherein said fasteners are isolated from the interior of said bag by said base.

12. The access fitting of claim 1 wherein said septum comprises an elongated strip longitudinally slidable between said open and closed positions.

13. The access fitting of claim 12 wherein said cap is provided with a guide channel in which said septum is slidably confined.

14. The access fitting of claim 1 wherein said tubular connector is detachable from said cap.

* * * * *